United States Patent [19]

Ebersole

[11] Patent Number: 4,522,786

[45] Date of Patent: Jun. 11, 1985

[54] MULTILAYERED TEST DEVICE FOR DETECTING ANALYTES IN LIQUID TEST SAMPLES

[75] Inventor: Richard C. Ebersole, Wilmington, Del.

[73] Assignee: E. I. Du Pont de Nemours and Company, Wilmington, Del.

[21] Appl. No.: 521,687

[22] Filed: Aug. 10, 1983

[51] Int. Cl.³ .................... G01N 21/78; G01N 33/52
[52] U.S. Cl. ........................ 422/56; 422/57; 435/805
[58] Field of Search .................. 422/55, 56, 57, 58, 422/60; 436/169, 170; 435/805

[56] References Cited

U.S. PATENT DOCUMENTS

| | | | |
|---|---|---|---|
| 3,420,205 | 1/1969 | Morison | 422/56 X |
| 3,723,064 | 3/1973 | Liotta | 23/234 R |
| 3,992,158 | 11/1976 | Przybylowicz et al. | 422/57 |
| 4,042,335 | 8/1977 | Clement | 23/253 TP |
| 4,144,306 | 3/1979 | Figueras | 422/56 |
| 4,166,093 | 8/1979 | Smith-Lewis et al. | 422/56 |
| 4,258,001 | 3/1981 | Pierce et al. | 422/56 |
| 4,288,228 | 9/1981 | Oberhardt | 422/56 X |

FOREIGN PATENT DOCUMENTS 0046004 2/1982 European Pat. Off. .
0066648 12/1982 European Pat. Off. .

Primary Examiner—Arnold Turk

[57] ABSTRACT

A foraminous septum, the foramina of which are filled with a thermally sensitive material, is used to form a barrier layer to separate two functional layers of a multilayered test device. At assay temperature, the septum prevents fluid communication between the functional layers. When heated, the thermally sensitive material melts allowing fluid communication between the functional layers.

The barrier layer can be used to control incubation and reaction times in multilayered test devices.

12 Claims, No Drawings

4,522,786

MULTILAYERED TEST DEVICE FOR DETECTING ANALYTES IN LIQUID TEST SAMPLES

FIELD OF THE INVENTION

This invention relates to an improved multilayered test device for detecting analytes in liquid test samples.

BACKGROUND OF THE INVENTION

Various types of chemical analyses have been used in the detection and measurement of various components of clinical interest in biological fluids. These analyses can be conveniently divided into two categories which are commonly labelled wet chemistry and dry chemistry. The wet chemistry analyses employ reagents in liquid solution and are widely used in both manual and automated analysis methods. The dry chemistry analyses employ reagents in substantially "dry-to-the-touch" test devices. Although both types of analyses have their advantages, the dry chemistry methods often are simpler in design, require less reagent manipulation, give quicker results and are more stable. Many dry chemistry methods have the disadvantage of being only qualitative, or, at best semi-quantitative, in their response to a given concentration of analyte, the compound to be measured in the biological fluid.

Several dry chemistry test devices which are capable of quantitative results have been described. In U.S. Pat. No. 4,042,335, issued to Clement on Aug. 16, 1977, a multilayered device for the analysis of liquids is described. The device includes (1) a reagent layer including a composition that is interactive in the presence of a predetermined analyte to provide a diffusible, detectable species, and (2) a registration layer that is permeable to the detectable species and within which such species can be detected. The element can include other layers which provide the radiation-blocking and for uniform spreading of the test sample. This test device can be used in the quantitative or qualitative analysis of biological fluids. However, the operational flexibility of this test device is severely limited: once liquid is applied, uncontrollable processing occurs by diffusion through the various layers. No means to control this diffusion is provided.

In U.S. Pat. No. 4,144,306, issued to Figueras on Mar. 13, 1979, a similar multilayered test device is disclosed. This test device can be used for immunochemical analysis. The layers can be spaced apart. Immediately after the test sample is applied, a compressive force can be applied to allow fluid contact among the previously separated layers. This test device provides no control of analyte or reagent migration through the layers after the sample is applied and the layers contacted.

U.S. Pat. No. 3,723,064, issued Mar. 27, 1973 to Liotta, describes a layered testing device for quantitatively determining the concentration of an analyte which includes a first or receiving layer impregnated with a chemical reagent for reaction with the analyte by which an end product is produced, a second or transmission layer to draw the end product through a porous membrane separating the first and second layers, and a third or indicator layer impregnated with reagents capable of reacting with the end product to provide a visual indication of the presence of the end product generated in layer one and reaching layer three. The indicator layer can be adapted to be peeled off and saved to provide a permanent record of the test. The porous mebrane interposed between the first and second layers has regions of different permeability which permit passage of the end product according to the concentration of the analyte. Passage of fluid through the porous membrane is solely a function of concentration of the analyte and is not otherwise controllable.

U.S. Pat. No. 4,258,001, issued Mar. 24, 1981 to Pierce et al., describes a multizone element for the analysis of substances in liquids which contains at least two permeable zones in direct fluid contact. No means are provided for controlling the diffusion of substances between zones after sample application.

U.S. Pat. No. 4,166,093, issued Aug. 28, 1979 to Smith-Lewis et al., describes an element for the analysis of liquids which contains a radiation-transmissive, detectable species migration-inhibiting layer interposed between a porous radiation-blocking layer and a radiation-transmissive reagent layer. All three layers are permeable to the analyte of interest. The migration-inhibiting layer acts solely to reduce the migration of the detectable species back into the radiation-blocking layer where it would be undetectable. That is, it functions as a one-way valve.

European Patent Application 0,046,004, published Feb. 17, 1982, describes a nonchromatographic assay device for the determination of members of an immunological pair. The device consists of at least two layers, an immunosorbing zone and a liquid absorbing zone in a liquid-receiving relationship. Additional layers can be involved which serve as barriers to inhibit migration of components of the signal producing system from the lower to the upper layer. The barrier is a chemical or enzymatic barrier and its structural integrity is not breached in the course of the assay.

European Patent Application No. 0,066,648, published Dec. 15, 1982, describes a dry-chemistry multilayer analysis element in which a competitive immune reaction is utilized for the detection of a specific component. One of the layers can be a timing layer, the function of which is to retain a sample solution in the reaction layer for a time sufficient to allow complete reaction of the sample with the detection reagents. The timing layer is typically composed of a polymeric material, preferably gelatin. It does not function as an all-or-none barrier to liquid flow, but merely controls the rate of that flow.

The multi-layered test devices described above share a common deficiency: Once the test sample is applied, the migration of analyte, reagents and reaction products becomes uncontrollable. The ability to migrate as well as the rate of migration are functions of the structure of the device. There is no way to (1) stop the migration of a particular species within a preselected layer of the device for the purpose of increasing the reaction time within that particular layer and (2) restart the migration into subsequent layers.

There is a need for a multilayered test device for chemical analysis in which one or more of the layers provides a means to stop or start the analyte and/or reagent migration through the layers once the test sample has been applied.

BRIEF SUMMARY OF THE INVENTION

This need is met in substantial measure by the present invention which is an improved multilayered test device for the analysis of analytes in test liquids. The improved device comprises at least two liquid permeable functional layers separated by a barrier layer comprising a chemically inert, liquid insoluble, foraminous septum, the foramina of which are filled with a thermally sensitive material which is liquid impermeable at assay temperature, but capable of melting when heated, thereby providing rapid liquid communication between said functional layers.

DETAILED DESCRIPTION OF THE INVENTION

A. In General

The multilayer device of this invention consists of combinations of two types of layers, functional and barrier layers. Each device will contain at least two functional layers and at least one barrier layer.

The barrier layer is used to separate physically two functional layers and to inhibit liquid communication between them until heat is applied to the barrier layer. The initial structural integrity of the barrier layer provides initial impermeability to fluid flow, but after application of heat and resultant loss of structural integrity of the barrier layer, liquid communication is provided between the functional layers.

B. Functional Layers

The functional layers can perform one or more of the following functions: distribution, separation, reaction, detection, shielding and incubation. At least two such layers, separated by the barrier layer, are present in the device of this invention. Various combinations of two or more of these functional layers, with or without additional barrier layers, can be constructed.

The structure and function of the various functional layers are taught extensively in U.S. Pat. No. 4,144,306, issued to Figueras on Mar. 13, 1979, which is incorporated herein by reference.

The reaction functional layer contains reagents for interaction with test sample components. Incubation of reagents in the reaction layer for a predetermined time (greater than that provided by diffusion) can be controlled by a properly timed application of heat to the thermally sensitive material in the barrier layer. The reaction layer is often used in conjunction with other functional layers. For example, enzyme immunoassays require an analyte-enzyme or an antibody-enzyme conjugate to be in a reaction layer. Upon application of the test sample, the analyte-enzyme conjugate (not a soluble reagent) and the free analyte from the test sample mix and compete for binding sites on an immobilized anti-analyte antibody. Upon application of heat, the fluid flows into a subsequent layer, thereby effecting the separation of free and bound analyte or enzyme-analyte. Thus, the first functional layer combines, in principle, both the reaction and separation functions. In this example, the subsequent layer can be a distribution layer which will also serve as a reaction and detection layer with reagents for the detection of the quantity of analyte-enzyme conjugate which permeates therein. Reagents in the functional layers can be either soluble or immobilized.

The detection layer (sometimes referred to as a registration layer) can perform several functions. The detection layer serves as the ultimate source for the detection of the analyte of interest. The detection layer can be a separate layer or it can be combined with the reaction or incubation layer. It can contain reagents necessary for the formation of a detectable signal or it can serve to concentrate the signal. The detection layer can also perform shielding functions. The detection layer, which is usually the bottommost functional layer of the device, can be permanently affixed to the test device or can be strippable from the device. If it is strippable, it can serve as a permanent record of the test result. The detection process may involve the visual observation of test sample components (e.g., red blood cells) or the visual or instrumental detection of products of an enzymatic or other chemical reaction. Other detection schemes include the visual or instrumental observation of aggregated latex particles or of colored pigment particles. Additionally, various instrumental means exist to detect the products of an enzymatic reaction, the analyte, or of various reaction products of the analyte. Often, a color will result which can be measured photometrically or reflectometrically. The products could be measured by their light scattering properties using turbidimetric or nephelometric techniques. Fluorescent products can be easily detected either visually or by use of instrumentation. The detection layer could also provide for the measurement of product through electrochemical means. Ion-selective electrodes can be used and are well known in the art for the measurement of ionic species. Amperometric detectors can be used for the detection of species such as $H_2O_2$ and for the detection of a wide variety of analytes which are capable of producing $H_2O_2$ when reacted with appropriate reagents.

The distribution layer, when present, can serve several purposes: It distributes the sample fluid uniformly across the surface area of the test device. It determines, by virtue of its thickness, the volume of sample fluid which is imbibed. And it can function to concentrate the analyte and remove interfering substances. A variety of paper and polymeric materials are suitable for fabrication of the distribution layer.

The separation functional layer serves to separate reagents and/or analyte during the performance of the test. One example of a separation layer is a controlled pore, size-exclusion gel layer which would separate materials, perhaps proteins from the test sample, on the basis of their molecular weight. Another example is the use of a separation layer with immobilized antibody or antigen to bind antigen or antibody respectively. After barrier layer destruction, these bound molecules would be separated from the other components in the sample which can then migrate into a subsequent layer.

The incubation layer, when present, functions as a holding zone. It may additionally contain immobilized or soluble reagents, in which case it also serves as a reaction layer. The incubation layer can also function as a reservoir for excess liquid.

The shielding layer, when present, functions to filter electromagnetic radiation. Most often this function is embodied in the support or base and does not constitute a separate layer.

C. Barrier Layer

The barrier layer serves to physically separate two functional layers and to prevent fluid communication between them until application of heat thereto.

Ideally, the barrier layer should act as an all-or-none barrier to fluid flow. At assay temperature, generally room temperature, there should be no fluid communication between the separated functional layers, while in its melted state there should be unimpeded communication. Therefore, it is desirable that once heat is applied, the permeability of the barrier layer increase rapidly.

The barrier layer of this invention can be made from a chemically inert, liquid insoluble, foraminous septum, the foramina of which are filled with a thermally sensitive material which is liquid impermeable at assay temperature, but capable of melting when heated above assay temperature. The melting process can include other phenomena such as solvation and swelling which tend to produce a physical change in the material leading to an opening of the foramina to fluid flow. As a practical matter, the barrier layer is designed such that at least about a 5° C. increase in temperature is required for melting. An increase of at least about 10° C. is preferred. The exact amount of heat required will depend on the exact nature of the barrier layer as well as assay material constraints.

Filtration materials are generally the most useful but not exclusively the only types of materials which can be used for the septum. These types of materials generally have well defined flow characteristics and low nonspecific binding properties. Filtration materials also are readily available. Furthermore, once the foramina have been opened, the sieving filtration properties of the filter can be used to advantage in some instances to remove interfering test substances and/or separate "free" and "bound" test materials such as encountered in immunoassay applications.

Specifically, there are four types of filter support matrices which have been found useful. The simplest types are constructed of net or woven materials such as nylon, synthetic polyester and natural fiber cloths. These materials generally have high strength and large pore sizes 50–1000μ, enabling the passage of large cells, and particulate solid phase reagents.

A second type of porous matrix which can be used are "depth filters". These are constructed of fibrous sheets or mats made of randomly arrayed fibers. These types of materials create a tortuous path which are useful in presenting high surface area and entrapping large particles down to 10μ. Such supports have been constructed of fibers of glass, paper, fur, silk, wool, hemp, jute, linen, metal, nylon, polyester, cellulose acetate, quartz and rubber materials.

A third type of matrix are the microporous membrane filters which have quite complex, open, colloidal type structures. These are made of various colloidal polymer films aand are commercially available from a variety of manufacturers. Most of the particle separations using the colloidal membrane filter matrices occur at the surface and not in the labyrinth of the internal channels. In some instances this presents an advantage since the solid phase can remain unincumbered by interfering particulates. However, colloidal membrane supports have relatively slow diffusion rates and for this reason are less preferred.

The fourth and most preferred type of matrix is a uniform pore membrane prepared from etching polycarbonate films with nuclear radiation. These supports, which are almost ideal sieves, have a true pore-like structure. These materials have very small void volumes. Impregnation thus forms a more secure fluid barrier. The membranes can thus be reduced in thickness without compromising the barrier properties. Furthermore, the uniform pore supports have intermediate flow properties which can be controlled to some extent by varying the pore diameter. For barrier applications, pore diameters in the range of 0.5 to 20μ are preferred. A further advantage of these types of supports is that minimal liquid is trapped within the void volume of the support and thus lost or not easily recovered. Furthermore these supports are commercially available with pore densities of $10^8$ to $10^9$ cm. This is adequate to permit rapid fluid communication through the barrier layer.

In addition to being a carrier for the thermally sensitive materials, the porous support matrix could be made to fulfill other important and essential test functions. These include (1) acting as a solid phase support for covalent or adsorbed test reagents; (2) acting as a "mordant sink" for the ionic or hydrophobic attachment of reaction materials (In this way, assay materials too small for filtration can be removed from the reaction mixture as it passes from one compartment to the next. In other words, by appropriate control over the chemical properties of the support, ionic and hydrophobic materials can be selectively removed from the test fluid as it passes from one compartment to the next. For example color dyes or interfering materials could be removed and prevented from entering the lower reaction compartments.); (3) sieving out or removing interfering particulates, cells or debris; (4) adjusting the flow rate between the layers.

A variety of thermally sensitive materials can be used for impregnation of the foraminous support in barrier layer preparation. Materials possessing a high degree of crystalline structure at room temperature, exhibiting a low melt index and not readily dissolvable by aqueous solution while in the crystalline state, but readily soluble in the unfolded or disassociated state are ideal materials.

For example several types of naturally occurring and synthetic polymeric materials exhibit ideal properties for this application.

(1) Polysaccharides of the family having 1,3 linked β-D-galactopyranose and 1,4 linked 3,6-anhydro-2-L-galactopyranose structures are suitable. For specific applications, the sugar residues can be substituted with sulfates, methoxyl, pyruvate and carboxyl groups. The materials known as agar or agarose can be highly purified and contain well defined melt and adsorption properties. For example, agarose with low charge content may be desirable to prevent non-specific binding. These materials are generally found in nature as extracts of algae or, in higher plants, as pectins.

(2) protein polymers of the gelatin or collagen family are also ideal polymeric materials.

(3) Synthetic polymers are believed to also possess similar physical properties and can be used in impregnating the septum for preparation of the barrier layer. These include vinyl-benzene, polyethylene oxides and polyvinyl alcohols.

These materials could be used both individually and/or in combination to vary the melt temperature of the thermally sensitive material.

The combination of particular septum material and thermoplastic polymer affects the temperature at which melting, and therefore permeability, occurs. For example, a nylon mesh impregnated with 5% gelatin became permeable at approximately 30° C., while filter paper impregnated with 5% gelatin became permeable at approximately 40° C.

In general, a solution of the polymer is made by dissolving the polymer in a liquid solvent such as phosphate buffered saline (PBS). The septum is dipped into the solution and then allowed to dry. This causes the foramina to the septum to become clogged, thereby rendering the septum liquid impermeable. The barrier layer is sandwiched generally contiguously between two functional layers. A preferred way of sandwiching the barrier layer between two functional layers is as follows: Two thin solid frames having cut-out sections in them, generally circular, are placed on top of one another with the barrier layer sandwiched between them and the cut-outs aligned. The assembly can be clamped together or adhesive can be used on the face of the two frames which contact the barrier layer. Absorbent material in the shape of the cut-out sections of the frame can be inserted within the cut-out sections to serve as functional layers. Generally, the assembly is then placed on a solid support to complete the test device. Application of heat to the barrier layer, for example by placing the test device on a constant temperature surface, causes the hardened polymer to melt, thereby opening the foramina to fluid flow. The foraminous nature of the septum can also serve to entrap the melted polymer thereby preventing occlusion of subsequent functional layers. The foraminous nature of the septum, once the polymer has been melted, causes capillary attraction of the test liquid through the septum and into the subsequent functional layer. The capillary attraction will allow the continued permeation of liquid independent of the direction of gravity.

D. Support Layer

The barrier and functional layers of the test device of this invention are generally disposed on a support layer which is impervious to fluid flow. The support layer can also serve such additional functions as facilitating handling and radiation shielding. It can be bonded to the device or strippable therefrom and it can be fabricated with or wihout entry ports. Some examples of suitable support materials are Mylar ®, ceramic, and alumina.

EXAMPLES

I. Permeability of the Barrier Layer as a Function of Temperature and Time

A 5% w/v solution of Roselott gelatin was prepared in PBS by heating. The solution was maintained at a temperature of approximately 15° C. above the solidification point. Samples of porous polycarbonate film, filter paper and nylon woven mesh were impregnated with the gelatin solution. The polycarbonate film was obtained from Bio-Rad Laboratories as an 8μ pore membrane sheet.

The supports were soaked until saturated with the gelatin solution and then removed and dried at room temperature for 4 hours. At this stage the supports were ready for use.

To test the barrier layer, 50 μL of an aqueous solution of blue dextran was applied to each of the gelatin treated supports.

At room temperature, no migration of dye solution was observed with the layers prepared with the 5% gelatin. Layers prepared with 0.5% gelatin did exhibit slow migration of the dye from the top layer to the bottom layers (within three hours).

The layers were then placed on a surface maintained at 60° C. The time required for the fluid to penetrate into the lower layer was determined. After 53 seconds of heating, the dye migrated through the polycarbonate barrier layer. After 1.2 minutes of heating, the dye migrated through the nylon barrier layer. After 5 minutes of heating, the dye migrated through the paper barrier layer.

By use of a thermocouple, the temperature of the barrier layers was determined as a function of time. After about 1 minute of heating using the 60° C. surface, the temperature of the barrier layer was roughly 33° C., while after 4 minutes, the temperature was roughly 45° C. This shows that the temperature to which the barrier layer must be raised to induce permeability is a function of the combination of the septum material and the thermally sensitive material.

II. Multilayered Test Device for Blood Typing

The test device was assembled from the following:

(1) An anti-type A receptor layer was prepared by equilibration of a nylon mesh activated with the aziridine cross-linking reagent XAMA-7 (Cordova Chemical Co.) with an aqueous solution (1 mg/mL) of anti-A lectin (Gamma Biologicals) for 8 hours at 21° C. The mesh was then washed free of excess lectin reagent by treatment with isotonic PBS at pH 7.4.

(2) The barrier layer was prepared by dipping a nylon mesh in a solution of 5% by weight Roselott gelatin. The mesh was then air dried for 24 hours before use.

(3) The adsorbent layer of the device was prepared from glass microfiber discs (Whatman GE/D) impregnated with $TiO_2$ particles which provided a visual barrier so that the red color of the cells entering the bottom layer would not be seen from the top of the device.

These three elements were then assembled together using support frames as described earlier.

To test the response of the device, a diluted sample (100 μL) of red blood cells (6% suspension in PBS buffer) was added to the anti-A layer. An additional 100 μL of PBS buffer wa then added. Following 10 minutes of equilibration, the device was warmed at 48° C. to open the barrier layer. The red cells not adsorbed to the top layer quickly passed into the lower chamber.

Visual inspection indicated that the nylon mesh had turned pink indicating successful red cell attachment. Scanning electron micrographs and photomicrographs confirmed attachment of red cells to the nylon.

III. Multilayered Test Device for Detecting Horseradish Peroxidase

Polyamide mesh discs (¾×0.002″) were treated first with aqueous methanol containing 10% w/v $CaCl_2$ and then treated with 3.65 M HCl for 30 minutes at 45° C. This hydrolyzed the polymer backbone and provided functional groups (COOH and $NH_2$) on the film surface for protein attachment. The film surface was then activated within a freshly prepared 5% aqueous solution of the trifunctional aziridine crosslinking reagent XAMA-7 (Cordova Chemical Co.) for 25 minutes at room temperature. Excess XAMA-7 reagent was removed by successive washes with purified water.

Protein attachment was then achieved by equilibrating the activated nylon discs in a saline (0.85%) solution containing 2 mg/mL anti-horseradish peroxidase antisera (Cappel Laboratories). (Rabbit IgG was used as control.) The films were then washed free of excess protein in cold phosphate-buffered saline (PBS) buffer, pH 7.5, and stored at 4° C. in PBS buffer until ready for use.

The barrier layer was prepared by impregnating the polycarbonate molecular filter (8.0μ, Bio Rad) with 5% aqueous Roselott gelatin as described above. The signal generating layers were prepared by saturating Whatman 54 filter paper discs with concentrated solutions containing o-phenylenediamine dihydrochloride and urea peroxide (25 mg) in bicarbonate buffer pH 5.0 (5.0 mL). The discs were quickly frozen at −40° C. and lyophilized.

The test device was assembled as follows: Rectangular frames were prepared by first cutting a ¾″ diameter hole in a plastic polyester sheet. Various thickness sheets were used depending on the reaction volume required for the test. The plastic layers were held together using double sided adhesive.

The test sample was prepared by diluting 1.1 mg of purified horseradish peroxidase in 100 mL of PBS buffer (0.01M, pH 7.4). Serial dilutions were then made in PBS buffer containing 0.8% (by weight) bovine serum albumin until a concentration of 1.1 ng/ml was prepared. 100 μL of this solution was then applied to each test element and equilibrated for 30 minutes at room temperature.

The test element was warmed to 48° C. at which time the barrier layer became permeable and rapid fluid migration occurred. PBS buffer (200 μL) was added to wash any residual "free" tag into the detection area and to solubilize the detection reagents. After five minutes of equilibration at room temperature the enzymatic chromogen development was visually observed through the bottom of the device.

To measure the "bound" enzyme tag fraction the first detection unit was removed. A second detection unit was attached. Chromogen substrate solution (100 μL) was added and the system equilibrated for five minutes. The barrier layer was opened as described above and response visualized through the support film.

I claim:

1. In a multilayered test device for the assay of analytes in test liquids, said device comprising at least two liquid permeable functional layers superposed upon one another, said layers being in liquid communication, the improvement comprising:

a barrier layer separating said layers, said barrier layer comprising a chemically inert, liquid insoluble, foraminous septum, the foramina of which are filled with a thermally sensitive material which is liquid impermeable at assay temperature, but capable of melting when heated, thereby providing rapid liquid communication between said functional layers.

2. The test device of claim 1 wherein the thermally sensitive material is selected from the group consisting of agar, agarose, gelatin, and collagen.

3. The test device of claim 2 wherein the thermally sensitive material is gelatin.

4. The test device of claim 1 wherein the thermally sensitive material is a vinyl-benzene, polyethylene oxide or polyvinyl alcohol synthetic polymer.

5. The test device of claim 1 wherein the foraminous septum is a net or woven material selected from the group consisting of nylon, synthetic polyester and natural fiber.

6. The test device of claim 5 wherein the woven material is nylon.

7. The test device of claim 1 wherein the foraminous septum is a mat made of randomly arranged fibers selected from the group consisting of paper, glass, fur, silk, wool, hemp, jute, linen, metal, nylon, polyester, cellulose acetate, quartz and rubber.

8. The test device of claim 7 wherein the fiber is paper.

9. The test device of claim 1 wherein the foraminous septum is a uniform pore membrane.

10. The test device of claim 9 wherein the membrane is a polycarbonate film etched with nuclear radiation.

11. The test device of claim 1 wherein the foraminous septum is an etched polycarbonate film and the thermally sensitive material is gelatin.

12. The test device of claim 11 wherein the gelatin is about 5% (w/v).

* * * * *